United States Patent
McClellan et al.

(10) Patent No.: US 9,539,004 B2
(45) Date of Patent: Jan. 10, 2017

(54) COLLAPSIBLE LOCKING SUTURE

(71) Applicant: Zone 2 Surgical, Inc., Morgantown, WV (US)

(72) Inventors: William Thomas McClellan, Morgantown, WV (US); Ephraim Akyuz, Logan, UT (US); David Skinlo, North Logan, UT (US)

(73) Assignee: ZONE 2 SURGICAL, INC., Morgantown, WV (US)

( * ) Notice: Subject to any disclaimer, the term of this patent is extended or adjusted under 35 U.S.C. 154(b) by 4 days.

(21) Appl. No.: 14/200,655

(22) Filed: Mar. 7, 2014

(65) Prior Publication Data

US 2014/0257379 A1 Sep. 11, 2014

Related U.S. Application Data

(60) Provisional application No. 61/774,867, filed on Mar. 8, 2013.

(51) Int. Cl.
*A61B 17/06* (2006.01)

(52) U.S. Cl.
CPC .......... *A61B 17/06166* (2013.01); *A61B 2017/06176* (2013.01); *A61B 2017/06185* (2013.01)

(58) Field of Classification Search
CPC . A61B 17/04; A61B 17/0483; A61B 17/0487; A61B 17/06; A61B 17/06166; A61B 2017/06176; A61B 2017/06185; A61B 2017/06171; B65B 13/32

(Continued)

(56) References Cited

U.S. PATENT DOCUMENTS

| 3,123,077 A | 3/1964 | Alcamo |
|---|---|---|
| 3,176,316 A | 4/1965 | Bodell |

(Continued)

FOREIGN PATENT DOCUMENTS

| WO | WO2011068533 | 6/2011 |
|---|---|---|
| WO | WO2013055886 | 4/2013 |
| WO | WO2014138570 | 9/2014 |

OTHER PUBLICATIONS

Ethicon, "An Exciting New Option for Tissue Control", Stratafix Knotless Tissue Control Device, 2012; 2 Pages.

(Continued)

*Primary Examiner* — Ryan J Severson
*Assistant Examiner* — Christian Knauss
(74) *Attorney, Agent, or Firm* — Andrew D. Wright; Roberts Mlotkowski Safran Cole & Calderon, P.C.

(57) ABSTRACT

A device including a self-locking suture including both a braided section and a monofilament section is provided. The monofilament includes a single strand. The braided section includes three or more strands that are intertwined or woven together. The terminal end of the braid is compressible to take on a radially expanded configuration. The braided structure is temporarily fixable in the open configuration providing a wide berth opening. A needle at the terminal end of the monofilament is insertable through the wide berth opening and pushed out through the back wall of the expanded braid, after which the braid can be pulled on to collapse it down onto the barbed monofilament. The construct may then be tightened onto the tissues to be joined, and the one-way locking mechanism between the braided trap and the directionally biased suture automatically engages. Another aspect includes a method of fastening tissue using the device.

13 Claims, 2 Drawing Sheets

(58) Field of Classification Search
USPC .................................. 100/29, 33 R, 33 PB
See application file for complete search history.

(56) References Cited

U.S. PATENT DOCUMENTS

| | | | |
|---|---|---|---|
| 3,541,591 A | 11/1970 | Hoegerman | |
| 3,545,008 A | 12/1970 | Bader, Jr. | |
| 3,570,497 A | 3/1971 | Lemole | |
| 3,664,345 A | 5/1972 | Dabbs et al. | |
| 3,805,300 A | 4/1974 | Tascon-Alonso et al. | |
| 3,833,200 A | 9/1974 | McCombs, Jr. | |
| 3,952,377 A | 4/1976 | Morell | |
| 3,976,079 A | 8/1976 | Samuels et al. | |
| 4,149,277 A | 4/1979 | Bokros | |
| 4,301,551 A | 11/1981 | Dore et al. | |
| 4,469,101 A | 9/1984 | Coleman et al. | |
| 4,535,764 A | 8/1985 | Ebert | |
| 4,688,561 A | 8/1987 | Reese | |
| 4,741,330 A | 5/1988 | Hayhurst | |
| 4,750,492 A | 6/1988 | Jacobs | |
| 4,950,284 A | 8/1990 | Green et al. | |
| 4,950,285 A | 8/1990 | Wilk | |
| 4,971,075 A | 11/1990 | Lee | |
| 4,979,956 A | 12/1990 | Silvestrini | |
| 5,053,047 A | 10/1991 | Yoon | |
| 5,061,283 A | 10/1991 | Silvestrini | |
| 5,123,913 A | 6/1992 | Wilk et al. | |
| 5,178,629 A * | 1/1993 | Kammerer | A61B 17/0469 606/148 |
| 5,207,694 A | 5/1993 | Broome | |
| 5,269,783 A | 12/1993 | Sander | |
| 5,314,436 A | 5/1994 | Wilk | |
| 5,318,566 A | 6/1994 | Miller | |
| 5,330,489 A | 7/1994 | Green et al. | |
| 5,356,412 A | 10/1994 | Golds et al. | |
| 5,356,417 A | 10/1994 | Golds | |
| 5,366,461 A | 11/1994 | Blasnik | |
| 5,372,146 A | 12/1994 | Branch | |
| 5,382,257 A | 1/1995 | Lewis et al. | |
| 5,391,173 A | 2/1995 | Wilk | |
| 5,403,346 A | 4/1995 | Loeser | |
| 5,413,585 A | 5/1995 | Pagedas | |
| 5,425,766 A | 6/1995 | Bowald | |
| 5,462,542 A | 10/1995 | Alesi | |
| 5,476,493 A | 12/1995 | Muff | |
| 5,520,691 A | 5/1996 | Branch | |
| 5,549,122 A | 8/1996 | Detweilwer | |
| 5,591,206 A | 1/1997 | Moufarrege | |
| 5,643,295 A | 7/1997 | Yoon | |
| 5,665,109 A | 9/1997 | Yoon | |
| 5,669,935 A | 9/1997 | Rosenman et al. | |
| 5,683,417 A * | 11/1997 | Cooper | 606/223 |
| 5,704,372 A | 1/1998 | Moll et al. | |
| 5,725,556 A | 3/1998 | Moser et al. | |
| 5,735,877 A | 4/1998 | Pagedas | |
| 5,741,301 A | 4/1998 | Pagedas | |
| 5,766,218 A | 6/1998 | Arnott | |
| 5,810,853 A | 9/1998 | Yoon | |
| 5,850,674 A | 12/1998 | Jansen | |
| 5,860,948 A | 1/1999 | Buscemi | |
| 5,972,006 A | 10/1999 | Sciaino | |
| 5,980,557 A | 11/1999 | Iserin et al. | |
| 5,984,933 A | 11/1999 | Yoon | |
| 6,007,576 A | 12/1999 | McClellan | |
| 6,014,792 A | 1/2000 | Marelin et al. | |
| 6,015,428 A | 1/2000 | Pagedas | |
| 6,063,106 A | 5/2000 | Gibson | |
| 6,066,160 A | 5/2000 | Colvin et al. | |
| 6,080,192 A | 6/2000 | Demopulos et al. | |
| 6,083,244 A | 7/2000 | Lubbers et al. | |
| 6,102,947 A | 8/2000 | Gordon | |
| 6,152,895 A | 11/2000 | Wilk | |
| 6,200,318 B1 | 3/2001 | Har-Shai et al. | |
| 6,296,659 B1 * | 10/2001 | Foerster | A61B 17/0469 606/224 |
| 6,423,123 B1 | 7/2002 | Rosenberg et al. | |
| 6,485,504 B1 | 11/2002 | Johnson et al. | |
| 6,514,265 B2 | 2/2003 | Ho et al. | |
| 6,695,855 B1 | 2/2004 | Gaston | |
| 6,740,100 B2 | 5/2004 | Demopulos et al. | |
| 6,913,607 B2 | 7/2005 | Ainsworth et al. | |
| 6,926,730 B1 | 8/2005 | Nguyen et al. | |
| 6,942,668 B2 | 9/2005 | Padget et al. | |
| 6,951,561 B2 | 10/2005 | Warren et al. | |
| 6,984,241 B2 | 1/2006 | Lubbers et al. | |
| 7,008,428 B2 | 3/2006 | Cachia et al. | |
| 7,226,468 B2 | 6/2007 | Ruff | |
| 7,255,700 B2 | 8/2007 | Kaiser et al. | |
| 7,335,215 B2 | 2/2008 | Buckman et al. | |
| 7,361,179 B2 | 4/2008 | Rousseau et al. | |
| 7,455,683 B2 | 11/2008 | Geissler et al. | |
| 7,601,165 B2 | 10/2009 | Stone | |
| 7,651,509 B2 | 1/2010 | Bojarski et al. | |
| 7,708,759 B2 | 5/2010 | Lubbers et al. | |
| 7,846,181 B2 | 12/2010 | Schwartz et al. | |
| 7,862,584 B2 | 1/2011 | Lyons et al. | |
| 7,959,650 B2 | 6/2011 | Kaiser et al. | |
| 8,109,968 B2 | 2/2012 | Ashley et al. | |
| 8,439,936 B2 | 5/2013 | McClellan | |
| 8,480,692 B2 | 7/2013 | McClellan | |
| 2002/0077631 A1 | 6/2002 | Lubbers et al. | |
| 2002/0161400 A1 | 10/2002 | Demopulos et al. | |
| 2002/0165561 A1 | 11/2002 | Ainsworth et al. | |
| 2002/0169359 A1 | 11/2002 | McCarthy et al. | |
| 2004/0059357 A1 | 3/2004 | Koseki | |
| 2004/0153104 A1 | 8/2004 | Buckman et al. | |
| 2004/0186515 A1 | 9/2004 | Rosenblatt | |
| 2004/0193217 A1 | 9/2004 | Lubbers et al. | |
| 2004/0267309 A1 | 12/2004 | Garvin | |
| 2005/0085833 A1 | 4/2005 | Gedebou | |
| 2005/0131430 A1 | 6/2005 | Ravikumar | |
| 2005/0149122 A1 | 7/2005 | McDevitt et al. | |
| 2006/0195103 A1 | 8/2006 | Padget et al. | |
| 2006/0276809 A1 | 12/2006 | Oliveira | |
| 2007/0021779 A1 | 1/2007 | Garvin et al. | |
| 2007/0055258 A1 | 3/2007 | Hansen | |
| 2008/0132943 A1 * | 6/2008 | Maiorino | A61B 17/06166 606/228 |
| 2009/0024216 A1 | 1/2009 | Cauthen, III et al. | |
| 2009/0221868 A1 | 9/2009 | Evans | |
| 2009/0228022 A1 | 9/2009 | McClellan | |
| 2009/0259251 A1 * | 10/2009 | Cohen | A61B 17/06166 606/228 |
| 2010/0268273 A1 | 10/2010 | Albertorio | |
| 2011/0022050 A1 | 1/2011 | McClellan et al. | |
| 2011/0029001 A1 | 2/2011 | Trieu et al. | |
| 2012/0046693 A1 | 2/2012 | Denham et al. | |
| 2012/0053630 A1 | 3/2012 | Denham et al. | |
| 2012/0143349 A1 * | 6/2012 | Peterson | A61B 17/06166 623/23.72 |
| 2012/0203253 A1 | 8/2012 | Kubiak | |
| 2012/0277770 A1 * | 11/2012 | Fenton et al. | 606/151 |
| 2014/0128888 A1 | 5/2014 | McClellan | |
| 2014/0257379 A1 | 9/2014 | McClellan | |
| 2014/0296887 A1 | 10/2014 | McClellan | |

OTHER PUBLICATIONS

Covidien, "Reduce Complications with V-Loc Wound Closure Device", http://ep.covidien.com/covidien-vloc-vloc..._source=google&utm_, 2013; 2 pages.
Angiotech, "Quill Redefining Wound Closure", http://www.md.angiotech.com/focus-markets/wound-closure/quill/, 2010; 3 Pages.
"Ethicon's New Stratafix Knotless Tissue Control Devices", http://www.medgadet.com/2012/10/ethicons-new-stratafix-knotless-tissue-control-devices.html/print/, Oct. 5, 2012, 3 pgs.
Covidien, "Announcing . . . The V-Loc 90.Absorbable Wound Closure Device", http://web.archive.org/web/20100917152329/http://www.covidien.com/vloc/pages.aspx, Sep. 17, 2010, 1 page.
Angiotech, "Quill Device", http://www.angiotech.com/focus-markets/wound-closure/quill/, 2011; 3 Pages.
Search Report and Written Opinion dated Mar. 21, 2013 for related PCT Application No. PCT/US2012/059705, 9 pages.

(56) References Cited

OTHER PUBLICATIONS

Search Report and Written Opinion dated Aug. 21, 2014 for related PCT Application No. PCT/US2014/021712, 8 pages.
Su,Wei-Ren et al., The Modified Finger-Trap Suture Technique: A Biomechanical Comparison of a Novel Suture Technique for Graft Fixation, Jan. 20, 2012, Abstract, 1 page.
Notice of Allowance from U.S. Appl. No. 14/068,425 dated Feb. 4, 2016; 9 pages.
Office Action from U.S. Appl. No. 14/350,874 dated Nov. 16, 2016; 10 pages.

* cited by examiner

COLLAPSIBLE LOCKING SUTURE

CROSS REFERENCE

This application claims priority to U.S. Provisional Patent Application No. 61/774,867, filed Mar. 8, 2013, the contents of which are incorporated by reference in their entirety.

FIELD OF THE INVENTION

The invention generally relates to medical devices, and more particularly to sutures and associated methods of manufacture and use.

BACKGROUND

Surgical suture is commonly used to join various tissues to each other. Suture commonly consists of a needle attached to a length of thread. The suture is passed through the tissues to be joined and a knot is typically tied to secure the final construct.

The ability to use a self-locking knotless suture may provide a number of advantages over conventional sutures. A knotless suture may provide the security of a knot while eliminating the bulk of a knot. Additionally, the ease of the procedure does not require the surgeon to learn new techniques. Further, the elimination of knot tying may increase the speed of the procedure potentially decreasing the time the patient is under anesthesia.

SUMMARY

In a first aspect of the invention, there is a device comprising a self-locking suture comprising both a braided section and a monofilament section. The monofilament comprises a single strand of a material. The braided section comprises three or more strands of material that are intertwined or woven together. The terminal end of the braid may be compressed such that it takes on a radially expanded configuration. The braided structure may be temporarily fixed in the open configuration that provides a wide berth opening. A needle at the terminal end of the monofilament may be inserted through the wide berth opening and pushed out through the back wall of the expanded braid. Once the needle is passed through the open braid, the braid can be pulled on to collapse it down onto the barbed monofilament. The construct may then be tightened onto the tissues to be joined, and the one-way locking mechanism between the braided trap and the directionally biased suture should automatically engage. Another aspect of the invention includes a method of fastening tissue using the device comprising the self-locking suture comprising both the braided section and the monofilament section.

In a another aspect of the invention, there is a method comprising: passing the needle of the device through the two sections of tissue to be joined together; introducing the tip of the needle into the temporarily fixed open braided trap section; and pushing the needle out through the back wall of the trap section, and feed the remaining portion of the needle through the trap. At this point the terminal end of the braided trap can be pulled on in order to lengthen and collapse the braided trap section down onto the monofilament. The method also comprises, with a counterforce being placed on the braided trap section, pulling on the needle end of the monofilament to tighten the suture loop onto the tissues. The one-way locking mechanism will automatically engage, thus no additional locking steps are required. The method further comprises cutting the free end of the monofilament near the point it exits the braided trap.

Implementations of the invention as described herein may be applicable in a manner similar to a suture, where various tissues may need to be joined together.

BRIEF DESCRIPTION OF THE SEVERAL VIEWS OF THE DRAWINGS

The present invention is described in the detailed description which follows, in reference to the noted plurality of drawings by way of non-limiting examples of exemplary embodiments of the present invention.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
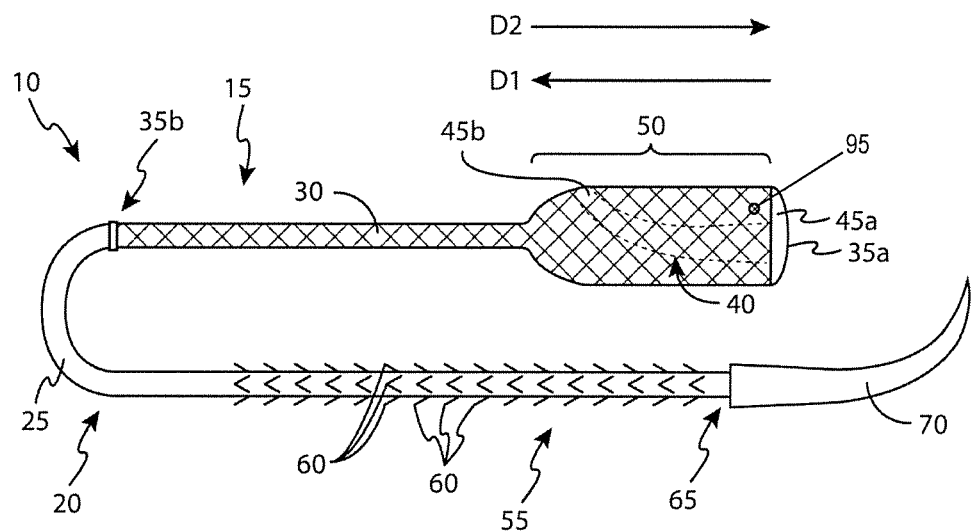
FIGS. 1, 2, 3a, 3b, and 4 show aspects of a collapsible locking suture and method of use in accordance with aspects of the invention.

FIG. 1 depicts a combination, self-locking suture 10. In embodiments, the self-locking suture 10 consists of both a braided section 15 and a monofilament section 20. In embodiments, the monofilament section 20 consists of a single strand of a material 25, while the braided section 15 consists of three or more strands of material 30 that are intertwined or woven together, e.g., in a helically wound braid. The braided material 30 may form a sheath of material strands with a hollow core. The braided material 30 and monofilament material 25 may or may not be the same material. Materials for the braided material 30 and monofilament material 25 may include but not limited to: non-resorbable polymers such as polyethylene, polyester, polypropylene or nylon; resorbable polymers such as polyglycolic acid, polylactic acid, or polydioxanone; biological materials such as catgut or silk; metals and any combination thereof.

The braided section 15 may be configured such that it can convert between two different states. The braided section 15 may change to a "collapsed" configuration as the ends 35a, 35b of the helically wound braid are pulled apart. This occurs as part of the normal behavior of a helically wound braid whereby the length of the helically wound braid increases as the diameter decreases when the ends are pulled. This occurs as the angles between the adjacent strands decreases at the crossing points, while simultaneously reducing the radial distance across the walls of the helically wound braid. The braided section 15 may also change to an "open" configuration as the two ends 35a, 35b of the helically wound braid are pushed towards each other, causing the length of the helically wound braid to decrease and the diameter to increase.

The terminal end 35a of the braided section 15 may have a passageway (e.g., tunnel) 40 created in it. The tunnel 40 begins at a first opening 45a in the hollow core at the end 35a of the braided section 15, and ends at a second opening

45b some distance from the first opening 45a and through the wall of the braided section 15. The first opening 45a may be created by fixing a portion of the braided section 15 in the "open" configuration, utilizing melting, gluing, welding or other similar operations. This process may help create a smooth entry point for the monofilament section 20 into the braided section 15 while eliminating any fraying that may occur from the ends of the fibers in the braid. The second opening 45b may be created by pushing aside the woven fibers of the braided material without cutting or disturbing the integrity of any of the fibers of the braided section 15. The second opening 45b may optionally be fixed in this "open" configuration using previously described techniques. Alternatively, the second opening 45b is not fixed in the open configuration. Between these two openings 45a, 45b is a free section 50 (also referred to as a braided trap) of the braided section 15 that can alter between the "open" and "collapsed" configurations as the braided section 15 is pushed together or pulled apart, respectively.

The free end 55 of the monofilament section 20 may have a number of directionally biased protrusions 60 (e.g., barbs) that extend axially and radially along the length of the free end 55 of the monofilament section 20. The directionally biased nature of the protrusions 60 allows for the monofilament section 20 to be inserted into the tunnel 40 of the braided section 15 in one direction D1, but engage the braided section 15 when the monofilament section 20 is pulled in the opposing direction D2. In embodiments, D1 and D2 are opposed axial directions. The tip 65 of the free end 55 of the monofilament section 20 may also be tapered or angled to facilitate the initial insertion through the tunnel of the braid. This tip 65 of the free end 55 may also have a needle 70 or other sharp tipped object that can easily penetrate tissue material.

Figure 2:
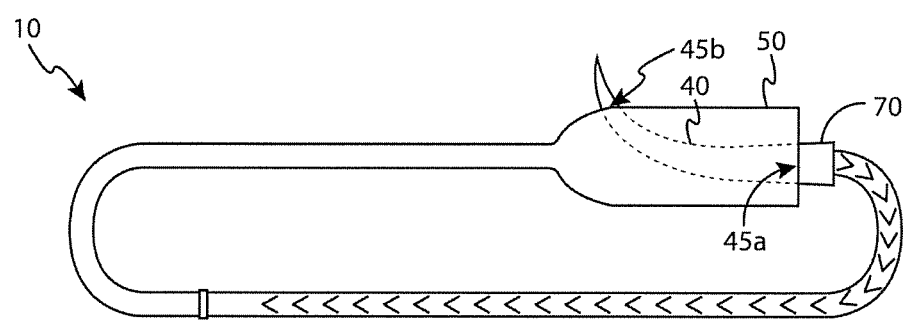
Figure 3A:
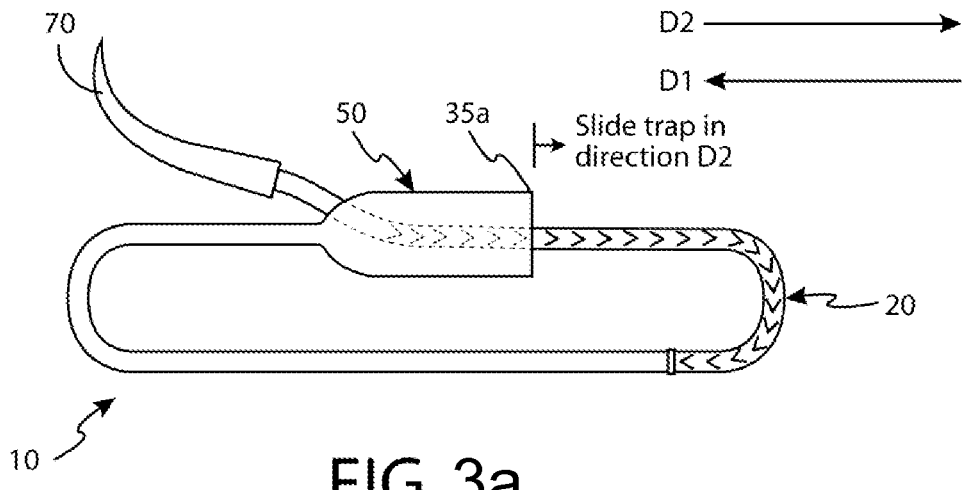
Figure 3B:
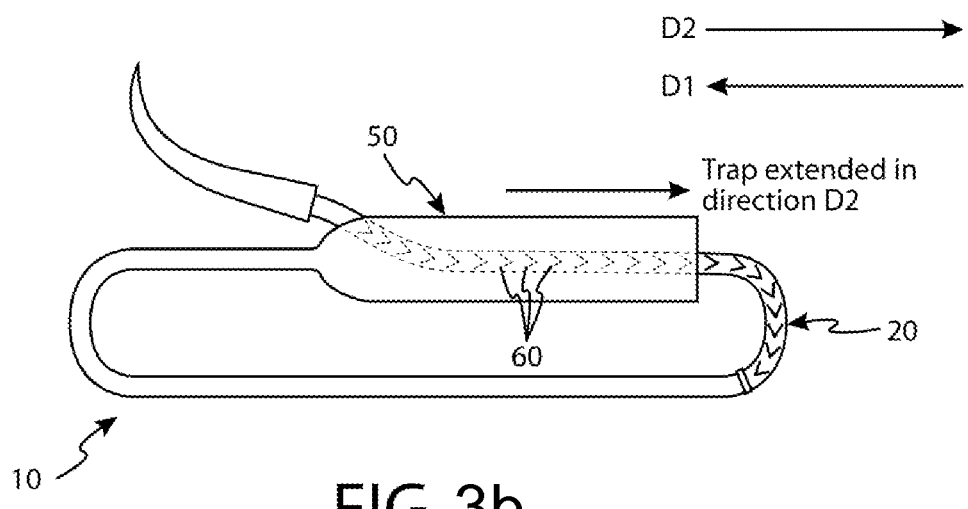
Figure 4:
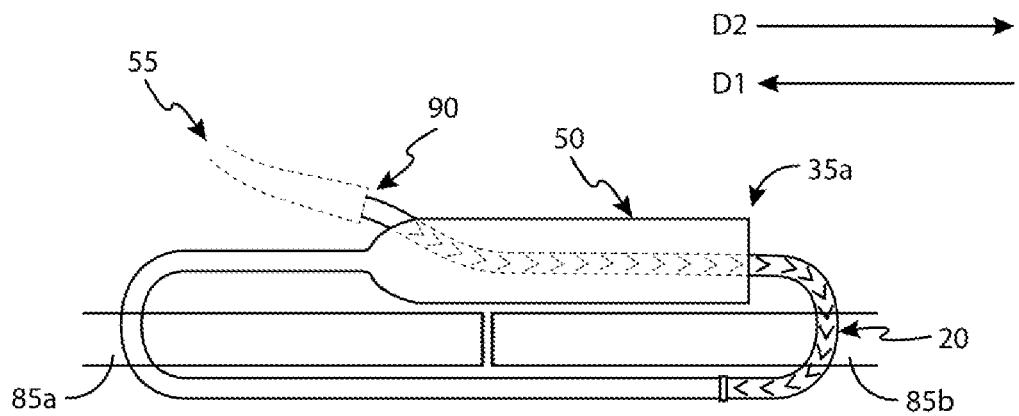

Once the free end 55 of the monofilament section 20 has been passed through the tissue(s) to be joined, the tip 65 of the monofilament is passed through the tunnel 40 of the braided trap 50, e.g., as depicted in FIG. 2. The resultant loop is shortened by pulling the free end 55 of the monofilament section 20 thereby tightening the tissues 85a, 85b together, e.g., as depicted in FIGS. 3a, 3b, and 4. A knot pusher or other instrument may be necessary to facilitate this tightening process. Once the desired level of tension is created in the loop, the remaining free end 55 of the monofilament section 20 may be cut off near the braided trap 50, e.g., as depicted at cut 90, as shown at FIG. 4.

In embodiments, the braided section 15 includes the braided trap 50 that may be temporarily fixed in the open configuration that provides a wide berth opening 45a, as shown in FIG. 1. A needle 70 at the terminal end of the monofilament section 20 may be inserted through the wide berth opening 45a and pushed out of opening 45b through the back wall of the expanded braided trap 50. Once the needle 70 is passed through the open braided trap 50, the braided section 15 can be pulled on (e.g., pulling end 35a in direction D2 and end 35b in direction D1) to collapse the braided trap 50 down onto the barbed monofilament 25, such that an inner surface of the braided trap 50 contacts an outer surface of the monofilament 25 at plural locations. The construct may then be tightened onto the tissues to be joined, and the one-way locking mechanism between the braided trap 50 and the directionally biased suture automatically engages.

The terminal end 35a of the braided section 15 may be compressed such that it takes on a radially expanded configuration, as shown in FIG. 1. This radially expanded configuration may be 2 times to 10 times the size (e.g., diameter) of the collapsed configuration (e.g., as shown in FIGS. 3b and 4), or more. This expansion may be accomplished by inserting a dowel pin inside the hollow core of the braided section 15. The dowel pin may have a tapered tip to facilitate insertion into the core of the braided section 15. While the braided section 15 is held in the open configuration over the dowel pin, a binding material 95 may be placed onto the expanded braided section 15. This binding material may comprise an adhesive or more specifically an elastic adhesive (such as a latex-based material). The adhesive may provide a temporary adhesion of the braid fibers in the open configuration, but the bonds may easily be broken by pulling on the braided section 15 (e.g., when collapsing the braided trap 50 onto the monofilament 20) without damaging or disrupting the fibers of the braid. Additionally the braided section 15 can be held in the expanded position by another specific radial braid or strand woven into the open braid. This may hold the receptacle braid open or otherwise influence the shape the that braid to accept a needle or male end of the suture.

The terminal end 35a of the open braided section 15 may further be fixed with a permanent adhesive that creates a stiff ring at the end of the braided section 15. This may be beneficial in that it provides a firm location that can be pulled on to break or stretch the elastic adhesive, allowing the braided trap 50 to collapse down to the collapsed configuration. Additionally, this stiff ring may be used to push the terminal end of the braided section 15 when cinching the suture onto the tissue. A secondary instrument such as a knot pusher may also be used to push against the stiff ring and extend the trap while cinching the device.

In aspects described herein, the exit portal 45b need not be fixedly formed. Instead, as the needle 70 is inserted into the expanded braided trap 50, the needle may be pushed out through the back end of the braided trap 50, e.g., between strands in the sidewall of the braid. This may help ease the manufacturing of the braided trap, as only an entry portal is provided.

Temporarily fixing the braid in this open configuration may help accomplish two different goals: (1) to provide a large target for insertion of the needle or free end of suture, (2) to shorten the length of the braided trap 50 to be initially threaded.

By significantly increasing the size of the expanded configuration, a larger target is created for which the needle or the terminal end of the monofilament can easily be inserted into. For instance, a Size 0 suture is approximately 0.35 mm in diameter, however, the braid may be expanded open to 2.0 mm or greater. This opening should be easily located by the tip of a typical needle used with suture, without the use of a microscope, loupe or supplemental visualization means. The large opening should not require enhanced dexterity that may be required for smaller openings.

Furthermore when the braided trap 50 is compressed into the open configuration, the overall length of the braided trap 50 is reduced. This reduced length may also increase the ease of which the needle or terminal end of the monofilament 20 can be inserted into the braided trap 50. For example, when the braided trap 50 is expanded to an open diameter of 2.0 mm, the length of the braided trap 50 may be 5 mm long; however when the braided trap 50 is collapsed down to a diameter of 0.35 mm, the length of the braided trap 50 may double or triple to 10-15 mm. The shortened length during the initial threading provides for ease of use, while the increased length may provide increased fixation strength of the construct by increasing the length of engagement of the trap to the monofilament 20.

FIGS. 2, 3*a*, 3*b*, and 4 show exemplary steps for using the collapsible locking suture 10 in accordance with aspects of the invention. Specifically, FIG. 2 depicts the needle 70 is pushed out the back wall of the braided trap 50. FIG. 3*a* depicts the braided trap 50 in its initial (expanded) configuration and FIG. 3*a* depicts the braided trap 50 in its extended (collapsed) configuration. FIG. 4 depicts the free end of the monofilament 20 is cut off to form the final construct across the adjoined tissue. In embodiments, a method of using the suture 10 includes the following steps.

1) Pass the needle 70 through the two sections of tissue 85*a*, 85*b* to be joined together.

2) Introduce the tip of the needle 70 into the temporarily fixed-open braided trap 50, e.g., at opening 45*a*.

3) Push the needle 70 out through the back wall of the braided trap 50, e.g., at opening 45*b*, and feed the remaining portion of the needle 70 through the braided trap 50, as shown in FIG. 2

4) At this point the terminal end 35*a* of the braided trap 50 is pulled in direction D2 in order to lengthen and collapse the braided trap 50 down onto the monofilament 20, as shown in FIGS. 3*a* and 4.

5) With a counterforce being placed on the braided trap 50, pull the needle end of the monofilament 20 to tighten the suture loop onto the tissues 85*a*, 85*b*, as shown in FIG. 4. The one-way locking mechanism will automatically engage, thus no additional locking steps are required.

6) Cut the free end of the monofilament 20 near the point it exits the braided trap 50, as shown in FIG. 4.

Alternatively, the collapsible braided trap may be provided as a separate entity from the barbed monofilament suture. A fully braided implant may be constructed with a collapsible trap arranged at each of the free ends.

Additional aspects of the invention include manufacturing the self-locking suture 10. The method of manufacturing may include: providing a suture including the braided section 15 and the monofilament section 20, and applying a binding material onto the expanded braided section 15 to temporarily retain the braided section 15 in the expanded configuration.

Even further aspects of the invention include providing instructions for using the self-locking suture 10, e.g., instructions for how to use the self-locking suture 10 in a method of attaching tissue as described herein. The instructions may be at least one of printed and video.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A device, comprising:
a self-locking suture comprising both a multifilament section and a monofilament section, wherein:
the monofilament section comprises a single strand of a material;
the multifilament section comprises three or more strands of material that are intertwined or woven together;
a first portion of the multifilament section at a terminal end of the multifilament in a radially expanded configuration, and a second portion of the multifilament section at another end of the multifilament section in a collapsed configuration, wherein the expanded configuration is larger in diameter than the collapsed configuration;
the multifilament section is temporarily fixable in the expanded configuration that provides a wide berth opening at the terminal end;
the multifilament section is collapsible onto the monofilament section after the monofilament section has been passed through the multifilament section;
a binding material that temporarily fixes the multifilament section in the expanded configuration,
wherein the binding material comprises an elastic adhesive;
the elastic adhesive provides a temporary adhesion of strands in the multifilament section in the expanded configuration: and
bonds of the elastic adhesive are breakable by pulling on the multifilament section without damaging the strands of the multifilament section.

2. The device of claim 1, wherein the monofilament section includes protrusions.

3. The device of claim 2, wherein the protrusions are directionally biased.

4. The device of claim 3, wherein the protrusions permit the monofilament section to be inserted into a tunnel of the multifilament section in a first direction, and engage the multifilament section when the monofilament section is pulled in a second direction opposing the first direction.

5. The device of claim 1, wherein the multifilament section is collapsible onto the monofilament section by pulling on the multifilament section.

6. The device of claim 1, wherein:
in the expanded configuration, the multifilament section has a first length and a first open diameter;
in a collapsed configuration, the multifilament section has a second length and a second open diameter;
the first length is less than the second length; and
the first diameter is greater than the second diameter.

7. The device of claim 1, wherein the multifilament section is a braided section.

8. The device of claim 7, further comprising a needle at a terminal end of the monofilament section that is insertable through the wide berth opening and configured to be pushed out of the braided section by moving the needle between strands of a sidewall of the braided section.

9. The device of claim 7, wherein the braided section comprises the three or more strands that are intertwined or woven together in a helically wound braid.

10. A method, comprising:
passing a needle of a suture device through two sections of tissue to be joined together;
introducing a tip of the needle into a temporarily fixed open braided trap of the suture device;

moving the needle out of the braided trap by moving the needle between strands of a sidewall of the braided trap, and feeding a remaining portion of the needle through the braided trap;

pulling on a terminal end of the braided trap in order to lengthen and collapse the braided trap down onto a monofilament of the suture device; and cutting a free end of the monofilament near a point where the monofilament exits the braided trap, wherein a binding material temporarily fixes the braided trap in the expanded configuration;

the binding material comprises an elastic adhesive that provides a temporary adhesion of strands in the braided trap in the expanded configuration; and bonds of the elastic adhesive are breakable by pulling on the braided trap without damaging the strands of the braided trap.

11. The method of claim 10, further comprising placing a counterforce on the braided trap and pulling the monofilament to tighten a loop of the suture device.

12. The method of claim 10, wherein, prior to the introducing, a terminal end of the braided trap is temporarily fixed in an expanded configuration that is larger than a collapsed configuration of the braided trap.

13. The method of claim 10, wherein the braided trap comprises three or more strands that are intertwined or woven together in a helically wound braid.

* * * * *